(12) United States Patent
Chen et al.

(10) Patent No.: US 10,376,688 B2
(45) Date of Patent: *Aug. 13, 2019

(54) NEUROSTIMULATOR INTERCONNECTION APPARATUS, SYSTEM, AND METHOD

(71) Applicant: Greatbatch Ltd., Clarence, NY (US)

(72) Inventors: Joey Chen, Valencia, CA (US); Leslie I. Halberg, Valencia, CA (US)

(73) Assignee: Greatbatch Ltd., Clarence, NY (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/355,117

(22) Filed: Nov. 18, 2016

(65) Prior Publication Data

US 2017/0065813 A1 Mar. 9, 2017

Related U.S. Application Data

(63) Continuation of application No. 14/316,960, filed on Jun. 27, 2014, now Pat. No. 9,539,422.
(Continued)

(51) Int. Cl.
*A61B 5/06* (2006.01)
*A61B 8/08* (2006.01)
(Continued)

(52) U.S. Cl.
CPC ............ *A61N 1/0551* (2013.01); *A61B 5/064* (2013.01); *A61B 8/0841* (2013.01); *A61N 1/05* (2013.01); *A61N 1/0553* (2013.01); *A61N 1/36017* (2013.01); *A61N 1/36021* (2013.01); *A61N 1/36071* (2013.01); *A61N 1/36125* (2013.01); *A61N 1/36139* (2013.01); *A61N 1/36146* (2013.01); *A61N 1/36153* (2013.01);
(Continued)

(58) Field of Classification Search
CPC ...... A61N 1/05; A61N 1/0551; A61N 1/0553; A61N 1/36; A61N 1/36017; A61N 1/36021; A61N 1/36071; A61N 1/36125; A61N 1/36139; A61N 1/36146; A61N 1/36153; A61N 1/37223; A61N 1/37235; A61N 1/37252; A61N 1/3752; A61N 1/3787; A61B 5/064; A61B 8/0841
USPC ................................ 607/9, 37, 116; 604/533
See application file for complete search history.

(56) References Cited

U.S. PATENT DOCUMENTS 3,522,575 A 8/1970 Johnson et al.
4,076,285 A 2/1978 Martinez et al.
(Continued)

*Primary Examiner* — Christopher A Flory
(74) *Attorney, Agent, or Firm* — Michael P. Horvath

(57) ABSTRACT

In various examples, an apparatus includes a neurostimulation interconnection apparatus including an elongate lead body including a lead proximal end and a lead distal end. The lead proximal end includes a first connector portion. A stimulation device includes a header. The header includes a second connector portion including a shape complementary to a shape of the first connector portion. The first connector portion is mateably engageable with the second connector portion, wherein one of the first connector portion and the second connector portion includes a plurality of pins and the other of the first connector portion and the second connector portion includes a plurality of sockets. There are an equal number of sockets and pins, wherein, with the first connector portion mateably engaged with the second connector portion, the pins align and electrically couple with the sockets.

20 Claims, 4 Drawing Sheets

Related U.S. Application Data

(60) Provisional application No. 61/841,965, filed on Jul. 2, 2013.

(51) Int. Cl.

| | | |
|---|---|---|
| *A61N 1/05* | (2006.01) | |
| *A61N 1/36* | (2006.01) | |
| *A61N 1/372* | (2006.01) | |
| *A61N 1/375* | (2006.01) | |
| *A61N 1/378* | (2006.01) | |

(52) U.S. Cl.
CPC ......... *A61N 1/3752* (2013.01); *A61N 1/3787* (2013.01); *A61N 1/37223* (2013.01); *A61N 1/37235* (2013.01); *A61N 1/37252* (2013.01)

(56) References Cited

U.S. PATENT DOCUMENTS

| | | |
|---|---|---|
| 4,187,846 A | 2/1980 | Carminucci et al. |
| 5,252,090 A * | 10/1993 | Giurtino .............. H01R 4/4818 439/441 |
| 5,662,696 A | 9/1997 | Kroll et al. |
| 5,733,151 A | 3/1998 | Edsall et al. |
| 5,906,634 A | 5/1999 | Flynn et al. |
| 6,198,969 B1 | 3/2001 | Kuzma |
| 6,516,227 B1 | 2/2003 | Meadows et al. |
| 6,609,029 B1 | 8/2003 | Mann et al. |
| 7,002,131 B1 | 2/2006 | Lewis et al. |
| 7,303,422 B2 | 12/2007 | Hoffer et al. |
| 7,347,746 B1 * | 3/2008 | He ........................ H01R 13/111 439/843 |
| 7,445,528 B1 * | 11/2008 | Kuzma ................ A61N 1/3752 439/369 |
| 7,526,339 B2 | 4/2009 | Lahti et al. |
| 7,727,183 B2 | 6/2010 | Sharon et al. |
| 7,736,191 B1 * | 6/2010 | Sochor ................ A61N 1/3752 439/668 |
| 7,794,256 B1 * | 9/2010 | Sochor ................ H01R 13/025 439/289 |
| 7,798,864 B2 | 9/2010 | Barker et al. |
| 8,100,019 B2 | 1/2012 | Moldenhauer et al. |
| 8,206,175 B2 | 6/2012 | Boyd et al. |
| 8,380,310 B2 | 2/2013 | Visco et al. |
| 8,401,649 B2 | 3/2013 | Tronnes et al. |
| 8,433,410 B2 | 4/2013 | Dabney et al. |
| 8,587,427 B2 | 11/2013 | Lalonde et al. |
| 8,639,354 B2 | 1/2014 | Bolea et al. |
| 8,700,160 B2 | 4/2014 | Berthin et al. |
| 2002/0038136 A1 | 3/2002 | Zaouali et al. |
| 2002/0108221 A1 * | 8/2002 | Miltich .................. A61N 1/375 29/25.41 |
| 2003/0040781 A1 * | 2/2003 | Larson .................. A61N 1/375 607/36 |
| 2003/0135246 A1 | 7/2003 | Mass et al. |
| 2003/0163171 A1 | 8/2003 | Kast et al. |
| 2004/0034392 A1 | 2/2004 | Spadgenske et al. |
| 2004/0106959 A1 * | 6/2004 | Schmidt ................ A61N 1/056 607/11 |
| 2005/0118887 A1 | 6/2005 | Hoffer et al. |
| 2005/0203584 A1 * | 9/2005 | Twetan ................ A61B 5/0031 607/36 |
| 2006/0167522 A1 | 7/2006 | Malinowski |
| 2006/0199432 A1 | 9/2006 | Taylor et al. |
| 2007/0055319 A1 | 3/2007 | Spadgenske et al. |
| 2007/0179555 A1 | 8/2007 | Iyer et al. |
| 2008/0009912 A1 | 1/2008 | Spadgenske et al. |
| 2008/0183225 A1 | 7/2008 | Adamski et al. |
| 2009/0243756 A1 | 10/2009 | Stevenson et al. |
| 2009/0266573 A1 * | 10/2009 | Engmark ............... A61N 1/375 174/50.54 |
| 2010/0285697 A1 | 11/2010 | Zart et al. |
| 2010/0331883 A1 | 12/2010 | Schmitz et al. |
| 2011/0004283 A1 | 1/2011 | Stevenson et al. |
| 2011/0022100 A1 | 1/2011 | Brase et al. |
| 2011/0149474 A1 * | 6/2011 | Sherwood ............. H01G 9/008 361/503 |
| 2011/0301665 A1 | 12/2011 | Mercanzini et al. |
| 2012/0095529 A1 | 4/2012 | Parramon et al. |
| 2012/0221074 A1 | 8/2012 | Funderburk et al. |
| 2012/0262250 A1 | 10/2012 | Stevenson et al. |
| 2012/0283806 A1 | 11/2012 | Troosters et al. |
| 2013/0023973 A1 | 1/2013 | Richard et al. |
| 2013/0123866 A1 | 5/2013 | McDonald |
| 2013/0288501 A1 * | 10/2013 | Russell ................ H01R 13/648 439/271 |
| 2013/0289683 A1 | 10/2013 | Parker et al. |
| 2013/0338750 A1 | 12/2013 | Eck et al. |
| 2014/0067020 A1 | 3/2014 | Kaula et al. |
| 2014/0107709 A1 | 4/2014 | Schmitz et al. |
| 2014/0128951 A1 * | 5/2014 | Kuntaegowdanahalli ................... A61N 1/05 607/116 |
| 2015/0043130 A1 * | 2/2015 | Sherwood ............. H01G 9/008 361/529 |

\* cited by examiner

NEUROSTIMULATOR INTERCONNECTION APPARATUS, SYSTEM, AND METHOD

CROSS REFERENCE TO RELATED APPLICATIONS

This application is a continuation of and claims the benefit of priority under 35 U.S.C. § 120 to U.S. patent application Ser. No. 14/316,960, now U.S. Pat. No. 9,539,422, filed on Jun. 27, 2014, entitled "NEUOROSTIMULATOR INTERCONNECTION APPARATUS, SYSTEM, AND METHOD," which claims the benefit of priority to U.S. Provisional Application Ser. No. 61/841,965, filed on Jul. 2, 2013, entitled "STIMULATION APPARATUSES, DEVICES, SYSTEMS, AND METHODS," each of which is incorporated by reference herein in its entirety.

TECHNICAL FIELD

The present patent document pertains generally to an interconnection apparatus, system, and method and more particularly, but not by way of limitation, to an interconnection apparatus, system, and method for use with a peripheral field stimulation device.

BACKGROUND

Implantable neurostimulators are an emerging area of healthcare. Advances in microelectronics, rechargeable power sources, and high-density mechanical systems have led to smaller, more robust, and cost-effective componentry for implantable devices. Stimulating lead technology has also improved, allowing for large numbers of contacts to be positioned near neural targets to improve selective activation and individually tailor therapy.

Lead connector technology, however, remains expensive and bulky compared to the other advanced components in neurostimulator systems. Most of the cost of a present-day multicontact neurostimulator is associated with lead connectors, and their size and volume limit package shape and shrinkability.

Overview

This overview is intended to provide an overview of subject matter of the present patent document. It is not intended to provide an exclusive or exhaustive explanation of the invention. The detailed description is included to provide further information about the present patent document.

The present inventor has recognized, among other things, that the subject matter can be used to couple components of a medical device. The present inventor has further recognized, among other things, that the subject matter can be used by an implantable stimulation system to couple a lead to a stimulator device. To better illustrate the apparatuses, systems, and methods described herein, a non-limiting list of examples is provided here:

Example 1 can include subject matter that can include a neurostimulation interconnection apparatus including an elongate lead body including a lead proximal end and a lead distal end. The lead proximal end includes a first connector portion. A stimulation device includes a header. The header includes a second connector portion including a shape complementary to a shape of the first connector portion. The first connector portion is mateably engageable with the second connector portion, wherein one of the first connector portion and the second connector portion includes a plurality of pins and the other of the first connector portion and the second connector portion includes a plurality of sockets. There are an equal number of sockets and pins, wherein, with the first connector portion mateably engaged with the second connector portion, the pins align and electrically couple with the sockets.

In Example 2, the subject matter of Example 1 is optionally configured such that the second connector portion includes the pins.

In Example 3, the subject matter of Example 2 is optionally configured such that the pins extend from the stimulation device as part of a feedthrough of the stimulation device.

In Example 4, the subject matter of any one of Examples 1-3 is optionally configured such that the pins are disposed in a substantially radial pattern.

In Example 5, the subject matter of any one of Examples 1-4 is optionally configured such that the pins are disposed in at least two substantially radial patterns.

In Example 6, the subject matter of any one of Examples 1-5 is optionally configured such that the pins are disposed in a substantially linear pattern.

In Example 7, the subject matter of any one of Examples 1-6 is optionally configured such that at least one of the first connector portion and the second connector portion includes a seal.

In Example 8, the subject matter of Example 7 is optionally configured such that the seal includes a seal protrusion extending outwardly from a perimeter of one of the first connector portion and the second connector portion. A seal groove is disposed within the other of the first connector portion and the second connector portion. The seal protrusion is complementary to and sealingly engageable within the seal groove with engagement of the first connector portion with the second connector portion.

In Example 9, the subject matter of any one of Examples 7-8 is optionally configured such that the seal includes a silicone barrier.

Example 10 can include, or can optionally be combined with any one of Examples 1-9 to include subject matter that can include a neurostimulation interconnection apparatus including an elongate lead body including a lead proximal end and a lead distal end. The lead proximal end includes a first connector portion. The first connector portion includes a connector plane. A stimulation device includes a header. The header includes a second connector portion including a shape complementary to a shape of the first connector portion. The first connector portion is mateably engageable with the second connector portion, wherein the first connector portion includes a plurality of first connectors and the second connector portion includes a plurality of second connectors. The plurality of first connectors are disposed along the connector plane. There are an equal number of first connectors and second connectors, wherein, with the first connector portion mateably engaged with the second connector portion, the first connectors align and electrically couple with the second connectors.

In Example 11, the subject matter of Example 10 is optionally configured such that the plurality of first connectors includes a plurality of sockets.

In Example 12, the subject matter of any one of Examples 10-11 is optionally configured such that the plurality of second connectors includes a plurality of pins.

In Example 13, the subject matter of Example 12 is optionally configured such that the pins extend from the stimulation device as part of a feedthrough of the stimulation device.

In Example 14, the subject matter of any one of Examples 10-13 is optionally configured such that the plurality of first connectors includes a plurality of printed contacts on a circuit board.

In Example 15, the subject matter of any one of Examples 10-14 is optionally configured such that the plurality of second connectors includes a plurality of conductor fingers.

In Example 16, the subject matter of any one of Examples 10-15 is optionally configured such that at least one of the first connector portion and the second connector portion includes a seal.

In Example 17, the subject matter of any one of Examples 10-16 is optionally configured such that a longitudinal axis of the lead body is substantially normal to the connector plane.

Example 18 can include, or can optionally be combined with any one of Examples 1-17 to include subject matter that can include a neurostimulation interconnection apparatus including an elongate lead body including a lead proximal end and a lead distal end. The lead proximal end includes a first connector portion. The first connector portion includes a connector plane, wherein a longitudinal axis of the lead body is substantially normal to the connector plane. A stimulation device includes a header. The header includes a second connector portion including a shape complementary to a shape of the first connector portion. The first connector portion is mateably engageable with the second connector portion, wherein the second connector portion includes a plurality of pins and the first connector portion includes a plurality of sockets. The plurality of sockets is disposed along the connector plane, there being an equal number of sockets and pins, wherein, with the first connector portion mateably engaged with the second connector portion, the pins align and electrically couple with the sockets.

In Example 19, the subject matter of Example 18 is optionally configured such that at least one of the first connector portion and the second connector portion includes a seal.

In Example 20, the subject matter of Example 19 is optionally configured such that the seal includes a seal protrusion extending outwardly from a perimeter of one of the first connector portion and the second connector portion. A seal groove is disposed within the other of the first connector portion and the second connector portion. The seal protrusion is complementary to and sealingly engageable within the seal groove with engagement of the first connector portion with the second connector portion.

DETAILED DESCRIPTION

The present patent document relates to apparatuses, systems, and methods for interconnecting components of an implantable device. In some examples, the apparatuses, systems, and methods described herein relate to interconnecting components of a peripheral field stimulation device. For instance, the apparatuses, systems, and methods of the present patent document are used, in some examples, to interconnect one or more lead bodies with a stimulation device.

The present inventor has recognized, among other things, that it is desirable to provide an interconnection apparatus or system that is relatively small and facilitates high-contact density connections. The present inventor has further recognized, among other things, that it is desirable to have a relatively easily manufacturable interconnection apparatus and system. While primarily described with respect to neurostimulation devices, it should be understood, however, that the subject matter described herein can be used with other implantable medical devices, as well as external devices in some examples.

As systems with more contacts evolve (for instance, driven by clinical need), the lack of advanced connectors becomes a roadblock for small, inexpensive systems. Various embodiments described herein include interconnection apparatuses and systems for implantable stimulators that feature one or more of high contact density, low cost, and long-term reliability. In particular, and in some embodiments, interconnection apparatuses and systems between the neurostimulator and stimulating leads are included.

Referring to FIGS. 1A-5, in some embodiments, it can be seen that the connector schemes are not in-line. That is, the example connector schemes include proximal contacts that are shown and described herein are not in-line and longitudinally spaced along a longitudinal axis of a proximal end of a lead body, as with typical stimulation leads that connect to a stimulation device via a bore.

Figure 1A:
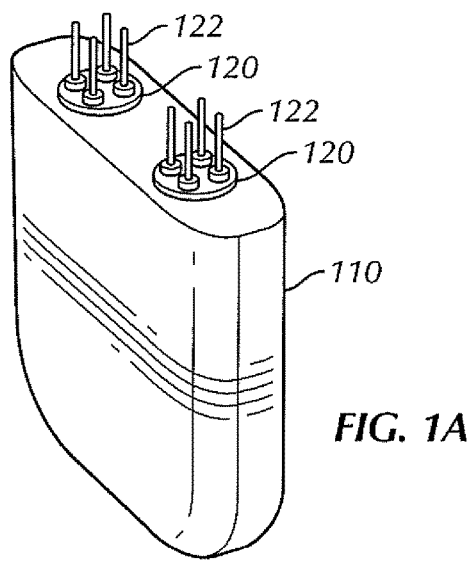
FIGS. 1A and 1B show an interconnection apparatus in accordance with at least one example of the invention.
Figure 1B:
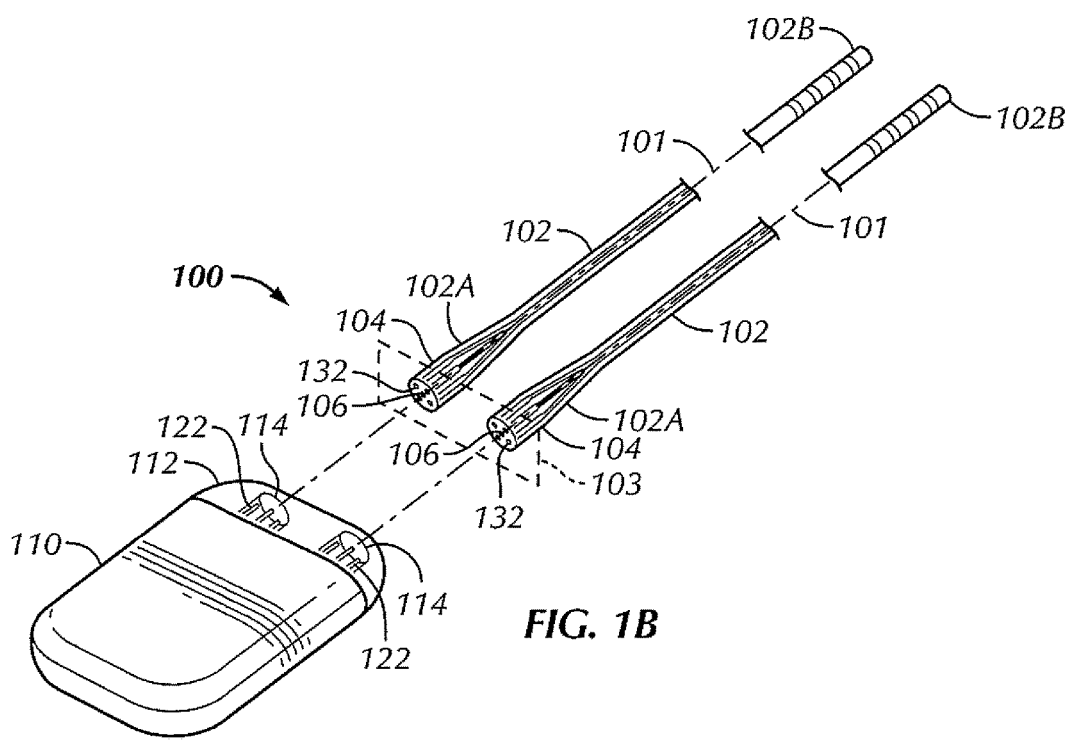

Referring to FIGS. 1A and 1B, in some examples, a neurostimulation interconnection apparatus 100 includes an elongate lead body 102 including a lead proximal end 102A and a lead distal end 102B. In some examples, the lead proximal end 102A includes a first connector portion 104. In some examples, a stimulation device 100 includes a header 112. In some examples, the header 112 includes a second connector portion 114 including a shape complementary to a shape of the first connector portion 104. In some examples, the first connector portion 104 is mateably engageable with the second connector portion 114. In some examples, the first connector portion 104 and the second connector portion 114 include complementary shapes that mate with one another in selective engagement. In some examples, the first connector portion 104 fits together with the second connector portion 114 with a snug fit. Although shown in FIGS. 1A and 1B with the first connector portion 104 fitting within the second connector portion 114, it should be understood that in other examples, the second connector portion fit within the first connector portion.

In some examples, one of the first connector portion 104 and the second connector portion 114 includes a plurality of first connectors 122, for instance, pins 122, and the other of the first connector portion 104 and the second connector portion 114 includes a plurality of second connectors 132, for instance sockets 132. In some examples, there are an equal number of sockets 132 and pins 122. In some examples, with the first connector portion 104 mateably engaged with the second connector portion 114, the pins 122 align and electrically couple with the sockets 132. Although shown in FIGS. 1A and 1B with the first connector portion 104 including the sockets 132 and the second connector portion 114 including the pins 122, it should be understood that, in other examples, the first connector portion can include the pins and the second connector portion can include the sockets. It is noted that the pins 122 and the sockets 132 are collectively called connectors 122, 132 herein. Additionally, although shown with pins 122 and mating sockets 132, it is within the spirit and scope of the present invention that other mating electrical connectors are used, such as, but not limited to conductor tabs and mating conductor fingers, as described herein.

In some examples, the first connector portion 104 includes a connector plane 103, wherein the plurality of second connectors 132 is disposed substantially along the connector plane 103. In some examples, a longitudinal axis 101 of the lead body 102 is substantially normal to the connector plane 103. In some examples, the second connectors 132 are all arranged at the lead proximal end 102A (and along the connector plane 103 normal to the longitudinal axis 101 of the lead body 102) rather than being disposed in line along the longitudinal axis 101 of the lead body 102.

In some examples in which the second connector portion 114 includes the pins 122, the pins 122 can extend from the stimulation device 110 as part of a feedthrough 120 of the stimulation device 110. That is, rather than making a separate connection (a weld, for instance) to attach the pins to the feedthrough, the pins 122 of the feedthrough 120 are used directly to interact with the sockets 132 of the first connector portion 104.

In some examples, the pins 122 are disposed in a substantially radial pattern. That is, the second connector portion 114 is substantially circular in shape with the pins 122 disposed around the second connector portion 114 in a substantially circular pattern. In some examples, the sockets 132 of the first connector portion 104 are similarly situated in a radial pattern to correspond to the pins 122 of the second connector portion 114. In some embodiments, the sockets 132 are radially oriented around a center lumen 106. In some examples, the lead body 102 includes the center lumen 106 disposed through the entire length of the lead body 102. In some embodiments, the connectors 122, 132 are arranged in a pattern that is arranged within a circle. In some examples, the pins 122 are disposed in at least two substantially radial patterns, for instance, to accommodate engagement of two lead bodies 102 with the two radial patterns of the pins 122. In various examples, more or fewer than two leads can be engaged with the stimulation device.

In some examples, appropriate connector keying can be done by the arrangement of the connectors 122, 132, mechanical detents, slotting, or the like, or any combination of such features. In some embodiments, visual and/or tactile clarity features can be included to indicate to the implanter how to connect the lead body 102 to the header 112. In some embodiments, the lead body 102 can be connected to the header 112 in any orientation, and internal firmware or programming software of the stimulation device 110 allows automatic or custom configuration as needed for each patient. In some embodiments, connector mating is pin-and-socket, although in other examples, other configurations are contemplated. In some embodiments, the pin 122 can be either in the lead body 102 or in the header 112 and the socket 132 can be the other of the lead body 102 and the header 112.

Figure 2A:
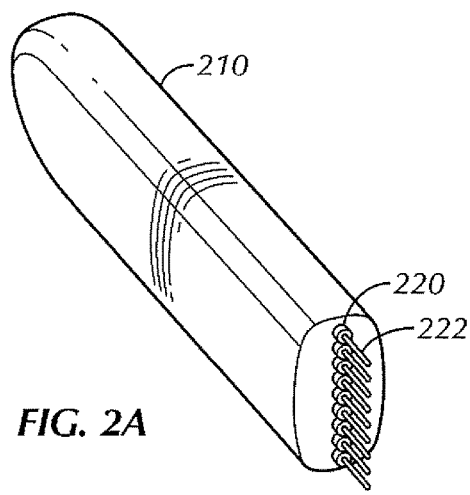
FIGS. 2A and 2B show an interconnection apparatus in accordance with at least one example of the invention.
Figure 2B:
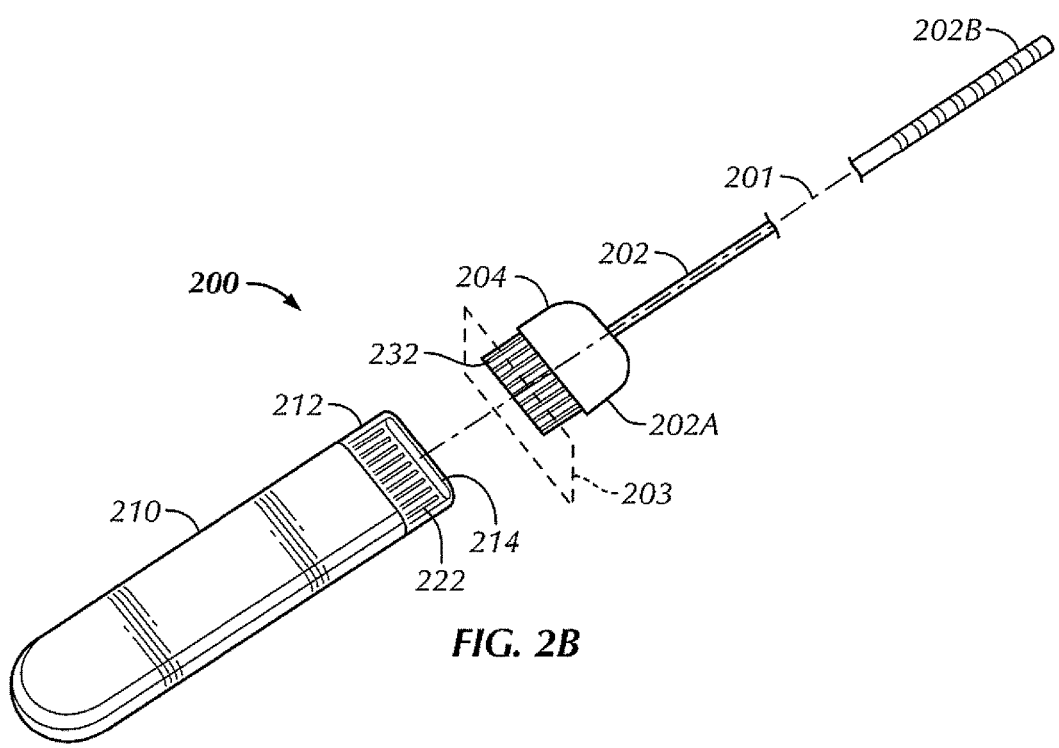

Referring to FIGS. 2A and 2B, in some examples, a neurostimulation interconnection apparatus 200 includes an elongate lead body 202 including a lead proximal end 202A and a lead distal end 202B. In some examples, the lead proximal end 202A includes a first connector portion 204. In some examples, a stimulation device 200 includes a header 212. In some examples, the header 212 includes a second connector portion 214 including a shape complementary to a shape of the first connector portion 204. In some examples, the first connector portion 204 is mateably engageable with the second connector portion 214. In some examples, the first connector portion 204 and the second connector portion 214 include complementary shapes that mate with one another in selective engagement. In some examples, the first connector portion 204 fits together with the second connector portion 214 with a snug fit. Although shown in FIGS. 2A and 2B with the first connector portion 204 fitting within the second connector portion 214, it should be understood that in other examples, the second connector portion fit within the first connector portion.

In some examples, one of the first connector portion 204 and the second connector portion 214 includes a plurality of first connectors 222, for instance, pins 222, and the other of the first connector portion 204 and the second connector portion 214 includes a plurality of second connectors 132, for instance, sockets 232. In some examples, there are an equal number of sockets 232 and pins 222. In some examples, with the first connector portion 204 mateably engaged with the second connector portion 214, the pins 222 align and electrically couple with the sockets 232. Although shown in FIGS. 2A and 2B with the first connector portion 204 including the sockets 232 and the second connector portion 214 including the pins 222, it should be understood that, in other examples, the first connector portion can include the pins and the second connector portion can include the sockets. It is noted that the pins 222 and the sockets 232 are collectively called connectors 222, 232 herein. Additionally, although shown with pins 222 and mating sockets 232, it is within the spirit and scope of the present invention that other mating electrical connectors are used, such as, but not limited to conductor tabs and mating conductor fingers, as described herein.

In some examples, the first connector portion 204 includes a connector plane 203, wherein the plurality of second connectors 232 is disposed substantially along the connector plane 203. In some examples, a longitudinal axis 201 of the lead body 202 is substantially normal to the connector plane 203. In some examples, the second connectors 232 are all arranged at the lead proximal end 202A (and along the connector plane 203 normal to the longitudinal axis 201 of the lead body 202) rather than being disposed in line along the longitudinal axis 201 of the lead body 202.

In some examples in which the second connector portion 214 includes the pins 222, the pins 222 can extend from the stimulation device 210 as part of a feedthrough 220 of the stimulation device 210. That is, rather than making a separate connection (a weld, for instance) to attach the pins to the feedthrough, the pins 222 of the feedthrough 220 are used directly to interact with the sockets 232 of the first connector portion 204.

In some examples, the pins 222 are disposed in a substantially linear pattern. That is, the second connector portion 214 is substantially linear or rectangular in shape with the pins 222 disposed along the second connector portion 214 in a substantially linear pattern. In some examples, the sockets 232 of the first connector portion 204 are similarly situated in a linear pattern to correspond to the pins 222 of the second connector portion 214. In some examples, the pins are disposed in at least two substantially linear patterns, for instance, to accommodate engagement of two lead bodies 202 with the two linear patterns of the pins 222. In various examples, more or fewer than two leads can be engaged with the stimulation device.

In some examples, appropriate connector keying can be done by the arrangement of the connectors 222, 232, mechanical detents, slotting, or the like, or any combination of such features. In some embodiments, visual and/or tactile clarity features can be included to indicate to the implanter how to connect the lead body 202 to the header 212. In some embodiments, the lead body 202 can be connected to the header 212 in any orientation, and internal firmware or programming software of the stimulation device 210 allows automatic or custom configuration as needed for each patient. In some embodiments, connector mating is pin-and-socket, although in other examples, other configurations are contemplated. In some embodiments, the pin 222 can be either in the lead body 202 or in the header 212 and the socket 232 can be the other of the lead body 202 and the header 212.

Figure 3:
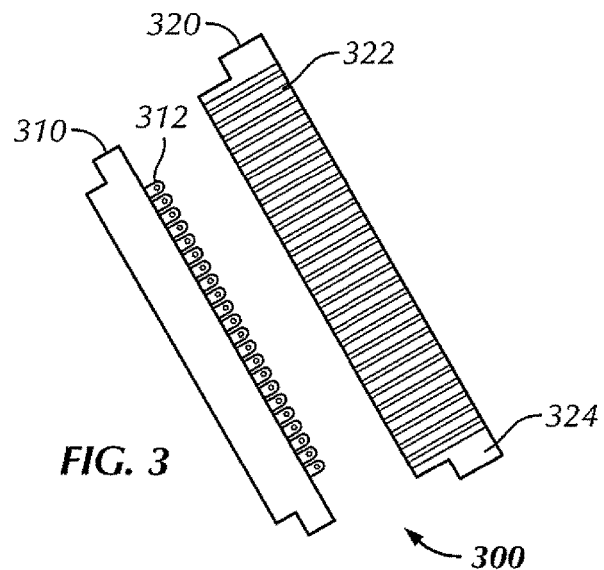
FIG. 3 shows components of an interconnection apparatus in accordance with at least one example of the invention.

Referring to FIG. 3, in some embodiments, an interconnection apparatus 300 (for instance, for use with one of the stimulation devices 100, 200 described herein) is edge-connector based. In some examples, the interconnection apparatus 300 includes a first connector portion 310 including one or more first connectors 312. In some examples, the one or more first connectors 312 are tabs formed from metal or another conductive material. In some examples, the interconnection apparatus 300 includes a second connector portion 320 including one or more second connectors 322. In some examples, the second connector portion 320 includes a printed circuit board 324 on which the one or more second connectors 322 are printed (as printed conductors, contacts, or traces, for instance) or otherwise formed. In some examples, this can allow for a high density of small electrical connector traces 322 to be formed using relatively inexpensive printed circuit or microelectronic fabrication techniques. In some examples, the one or more conductor tabs 312 are disposed in a manner to make and maintain electrical contact with the one or more connector traces 322 with the first connector portion 310 and the second connector portion 320 mateably engaged. In further examples, the one or more conductor tabs 312 can be biased to maintain contact with the one or more connector traces 322 with the first connector portion 310 mateably engaged with the second connector portion 320. In some examples, connector mating can also include conductor tabs and conductor fingers, where the fingers are preferably formed by a small bent piece of metal that deflects when the connector is inserted and makes a spring contact to the conductor tab. In various examples, other mating connectors are contemplated, including pin and socket connectors, as are described herein.

Figure 4A:
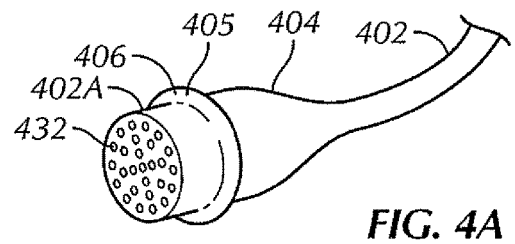
FIGS. 4A and 4B show an interconnection apparatus in accordance with at least one example of the invention.
Figure 4B:
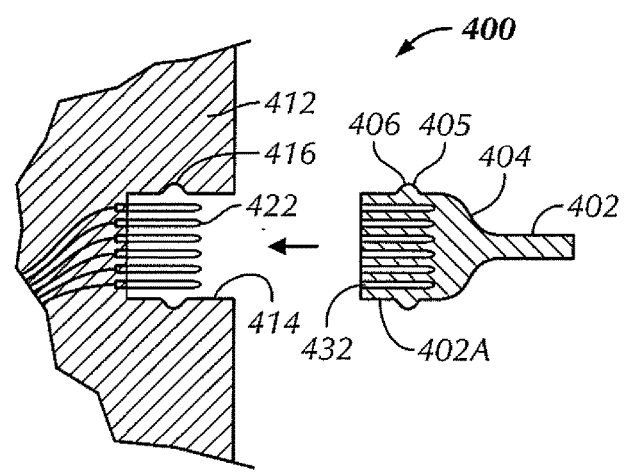

Referring to FIGS. 4A and 4B, in some examples, an interconnection apparatus 400 includes a first connector portion 404 disposed at a proximal end 402A of a lead body 402 configured to mateably engage with a second connector portion 414 of a header 412. In some examples, the interconnection apparatus 400 can be used with the stimulation devices 110, 210 and the lead bodies 102, 202 described herein. In some examples, the first connector portion 404 includes one or more sockets 432 and the second connector portion 414 includes a corresponding number of pins 422, with the first connector portion 404 configured to mateably engage with the second connector portion 414 to electrically couple the one or more pins 422 with the one or more sockets 432. In other examples, other connector schemes can be used other than a pin-and-socket scheme, such as, but not limited to an edge-connector based scheme like the interconnection apparatus 300 described herein.

In some examples, the first connector portion 404 and the second connector portion 414 can have a sealing mechanism, for instance, to keep out body fluids that might compromise the electrical isolation. In some examples, at least one of the first connector portion 404 and the second connector portion 414 includes a seal 405. In some examples, the seal 405 includes a seal protrusion 406 extending outwardly from a perimeter of one of the first connector portion 404 and the second connector portion 414. In some examples, a seal groove 416 is disposed within the other of the first connector portion 404 and the second connector portion 414. In some examples, the seal protrusion 406 is complementary to and sealingly engageable within the seal groove 416 with engagement of the first connector portion 404 with the second connector portion 414. In some examples, the seal 405 or the seal protrusion 406 includes a silicone barrier. That is, in some embodiments, a first-line sealing mechanism is a ring of silicone protrusively molded on the outer part of the first connector portion 404, such that, once inserted into the second connector portion 414, it provides a press-fit seal along the outer perimeter of the first connector portion 404. In some embodiments, the seal groove 416 can include a detent within the inner portion of the second connector portion 414 in which the silicone sealing protrusion 406 rests. Such a configuration, in some examples, can provide more consistent sealing as well as a degree of tactile feedback for insertion and removal.

Figure 5:
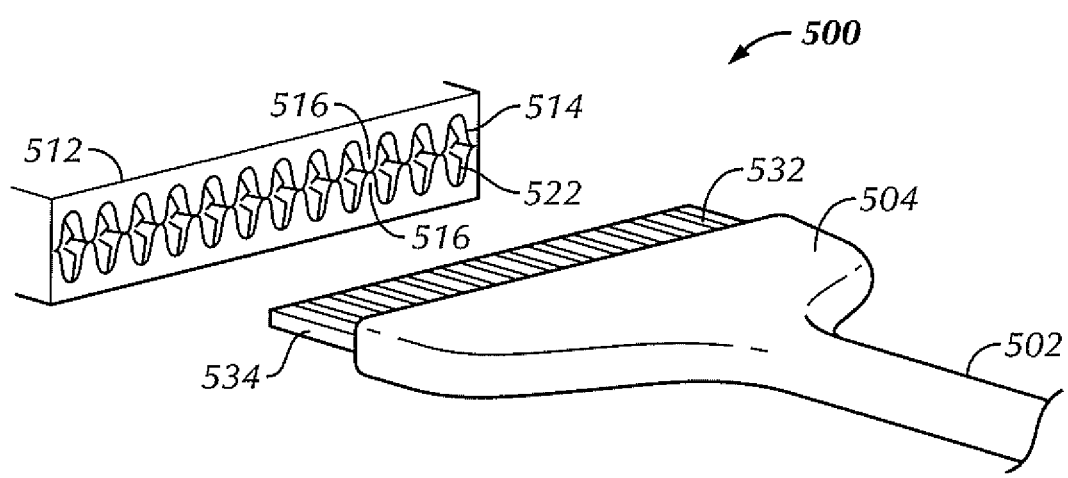
FIG. 5 shows an interconnection apparatus in accordance with at least one example of the invention.

Referring to FIG. 5, in some examples, an interconnection apparatus 500 includes a first connector portion 504 disposed at a proximal end 502A of a lead body 502 configured to mateably engage with a second connector portion 514 of a header 512. In some examples, the interconnection apparatus 500 can be used with the stimulation devices 110, 210 and the lead bodies 102, 202 described herein. In some examples, the first connector portion 504 includes an edge-connector based scheme like the interconnection apparatus 300 described herein. In some examples, the first connector portion 504 includes one or more first connectors 532. In some examples, the first connector portion 504 includes a printed circuit board 534 on which the one or more second connectors 532 are printed (as printed conductors, contacts, or traces, for instance) or otherwise formed. In some examples, this can allow for a high density of small electrical connector traces 532 to be formed using relatively inexpensive printed circuit or microelectronic fabrication techniques. In some examples, the one or more second connectors 522 are tabs formed from metal or another conductive material. In some examples, the one or more conductor tabs 522 are disposed in a manner to make and maintain electrical contact with the one or more connector traces 532 with the first connector portion 504 and the second connector portion 514 mateably engaged. In further examples, the one or more conductor tabs 522 can be biased to maintain contact with the one or more connector traces 532 with the first connector portion 504 mateably engaged with the second connector portion 514. In some examples, connector mating can also include conductor tabs and conductor fingers, where the fingers are preferably formed by a small bent piece of metal that deflects when the connector is inserted and makes a spring contact to the conductor tab. In various examples, other mating connectors are contemplated, including pin and socket connectors, as are described herein. In some embodiments, one or more sealing barriers 516 can be included between individual conductors tabs 522. For example, in some examples, each conductor tab 522 can include a silicone barrier 516 between it and adjacent conductor tabs 522. In some examples, with the first connector portion 504 mateably engaged with the second conductor portion 514, the sealing barriers 516 press against the printed circuit board 534 between each of the connector traces 532 to electrically isolate each paired connector trace 532/conductor tab 522 coupling from each other paired connector trace 532/conductor tab 522 coupling.

In some examples, the interconnection apparatuses 100, 200, 300, 400, 500 can include low electrical impedance. In some examples, the electrical impedance is less than 1 Ohm. In some examples, the interconnection apparatuses 100, 200, 300, 400, 500 are configured such that the impedance of the connection does not change under flexion, tension, or deflection.

In some examples, the interconnection apparatuses 100, 200, 300, 400, 500 can be characterized by zero- or low-insertion forces, with tactile, visual, and/or audible feedback being provided that may be, by way of example, loud enough to hear in a busy operating room, when the interconnection apparatus 100, 200, 300, 400, 500 is fully seated. This can provide the user with confidence that a suitably mated connection has been achieved.

In some embodiments, each of the interconnection apparatuses 100, 200, 300, 400, 500 has a locking mechanism. In some embodiments, once the interconnection apparatus 100, 200, 300, 400, 500 is seated, the user actuates a mechanism that is configured to provide tactile, visual, and/or audible feedback to confirm that a threshold of acceptability and robustness for the connection has been established.

In some embodiments, the interconnection apparatuses 100, 200, 300, 400, 500 described herein can be advantageous in that they can eliminate expensive connector block systems in IPGs by replacing them with pin-and-socket, edge-connector, or other configurations. Such advantages may include, but are not limited to, high density, low cost, "single" connections, which can be configured to provide lower insertion forces, be self-locking, provide nicely controlled insertion forces, and have a single outer seal (or individual seals per pin, for pin-and-socket connectors). In some embodiments, connector stack alignment and parts complexity issues can be lessened if not eliminated, leading to easier assembly and/or lower cost. In some embodiments, this can be advantageous in surgical applications, in which, for example, a health care provider is not required to fit a lead down and through a needle.

The present inventor has recognized various advantages of the subject matter described herein. For instance, in some examples, the apparatuses, systems, and methods described herein can be used to provide an interconnection apparatus or system that is relatively small and facilitates high-contact density connections. In various examples, the apparatuses, systems, and methods described herein are considered advantageous in that they allow for relatively easily manufacturability. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A neurostimulation interconnection apparatus comprising:
    an elongate lead body including a lead proximal end and a lead distal end, the lead proximal end including a first connector portion; and
    a stimulation device including a header, the header including a second connector portion including a shape complementary to a shape of the first connector portion, the first connector portion being mateably engageable with the second connector portion, wherein at least one of the first connector portion and the second connector portion includes a substrate including a plurality of connectors disposed on the substrate, and the other of the first connector portion and the second connector portion includes a plurality of conductor tabs, there being an equal number of connectors and conductor tabs, wherein, with the first connector portion mateably engaged with the second connector portion, the connectors align and electrically couple with the conductor tabs, wherein at least one of the first connector portion and the second connector portion includes a seal, the seal including:
        a seal protrusion extending entirely around and outwardly from a perimeter of one of the first connector portion and the second connector portion; and a seal groove disposed within and extending entirely around the other of the first connector portion and the second connector portion, the seal protrusion being complementary to and sealingly engageable within the seal groove with engagement of the first connector portion with the second connector portion.

2. The neurostimulation interconnection apparatus of claim 1, wherein the plurality of connectors includes a plurality of printed conductors printed on the substrate.

3. The neurostimulation interconnection apparatus of claim 2, wherein the plurality of printed conductors includes a plurality of traces.

4. The neurostimulation interconnection apparatus of claim 1, wherein the plurality of connectors includes a plurality of conductor fingers, wherein, with engagement of the first connector portion and the second connector portion, each of the conductor fingers is configured to deflect to make spring contact with the corresponding conductor tab.

5. The neurostimulation interconnection apparatus of claim 1, wherein the substrate includes a printed circuit board.

6. The neurostimulation interconnection apparatus of claim 1, wherein the conductor tabs are biased in a direction to maintain contact with the connectors with the first connector portion mateably engaged with the second connector portion.

7. The neurostimulation interconnection apparatus of claim 1, wherein the conductor tabs are formed from metal.

8. The neurostimulation interconnection apparatus of claim 1, wherein the substrate and the plurality of connectors disposed on the substrate are disposed in a substantially linear configuration.

9. The neurostimulation interconnection apparatus of claim 1, wherein the seal protrusion includes a silicone protrusion.

10. The neurostimulation interconnection apparatus of claim 1, wherein the seal protrusion is integrally formed with one of the first connector portion and the second connector portion.

11. The neurostimulation interconnection apparatus of claim 1, comprising a plurality of sealing barriers, wherein, with engagement of the first connector portion with the second connector portion, the sealing barriers are configured to press against the substrate between each of the connectors to electrically isolate each paired connector and conductor tab from each other paired connector and conductor tab.

12. A neurostimulation interconnection apparatus comprising:
an elongate lead body including a lead proximal end and a lead distal end, the lead proximal end including a first connector portion; and
a stimulation device including a header, the header including a second connector portion including a shape complementary to a shape of the first connector portion, the first connector portion being mateably engageable with the second connector portion, wherein at least one of the first connector portion and the second connector portion includes a substrate including a plurality of printed traces printed on the substrate, and the other of the first connector portion and the second connector portion includes a plurality of conductor tabs, there being an equal number of printed traces and conductor tabs, wherein, with the first connector portion mateably engaged with the second connector portion, the printed traces align and directly electrically couple with the conductor tabs.

13. The neurostimulation interconnection apparatus of claim 12, wherein the substrate includes a printed circuit board.

14. The neurostimulation interconnection apparatus of claim 12, wherein the conductor tabs are biased in a direction to maintain contact with the printed traces with the first connector portion mateably engaged with the second connector portion.

15. The neurostimulation interconnection apparatus of claim 12, wherein the substrate and the plurality of printed traces disposed on the substrate are disposed in a substantially linear configuration.

16. The neurostimulation interconnection apparatus of claim 12, wherein at least one of the first connector portion and the second connector portion includes a seal, the seal including:
a seal protrusion extending entirely around and outwardly from a perimeter of one of the first connector portion and the second connector portion; and
a seal groove disposed within and extending entirely around the other of the first connector portion and the second connector portion, the seal protrusion being complementary to and sealingly engageable within the seal groove with engagement of the first connector portion with the second connector portion.

17. The neurostimulation interconnection apparatus of claim 12, comprising a plurality of sealing barriers, wherein, with engagement of the first connector portion with the second connector portion, the sealing barriers are configured to press against the substrate between each of the printed traces to electrically isolate each paired printed trace and conductor tab from each other paired printed trace and conductor tab.

18. A neurostimulation interconnection apparatus comprising:
an elongate lead body including a lead proximal end and a lead distal end, the lead proximal end including a first connector portion; and
a stimulation device including a header, the header including a second connector portion including a shape complementary to a shape of the first connector portion, the first connector portion being mateably engageable with the second connector portion, wherein one of the first connector portion and the second connector portion includes a printed circuit board including a plurality of printed traces printed on the printed circuit board, and the other of the first connector portion and the second connector portion includes a plurality of conductor tabs, there being an equal number of printed traces and conductor tabs, wherein, with the first connector portion mateably engaged with the second connector portion, the printed traces align and directly electrically couple with the conductor tabs, the conductor tabs being biased in a direction to maintain contact with the connectors, wherein the printed circuit board and the plurality of printed traces disposed on the printed circuit board are disposed in a substantially linear configuration.

19. The neurostimulation interconnection apparatus of claim 18, wherein at least one of the first connector portion and the second connector portion includes a seal, the seal including:
a seal protrusion extending entirely around and outwardly from a perimeter of one of the first connector portion and the second connector portion; and
a seal groove disposed within and extending entirely around the other of the first connector portion and the second connector portion, the seal protrusion being complementary to and sealingly engageable within the seal groove with engagement of the first connector portion with the second connector portion.

20. The neurostimulation interconnection apparatus of claim 18, comprising a plurality of sealing barriers, wherein, with engagement of the first connector portion with the second connector portion, the sealing barriers are configured to press against the printed circuit board between each of the printed traces to electrically isolate each paired printed trace and conductor tab from each other paired printed trace and conductor tab.

* * * * *